(12) United States Patent
Pohan

(10) Patent No.: US 7,075,089 B2
(45) Date of Patent: Jul. 11, 2006

(54) DETECTOR FOR AN X-RAY COMPUTER TOMOGRAPH

(75) Inventor: Claus Pohan, Baiersdorf (DE)

(73) Assignee: Siemens Aktiengesellschaft, Munich (DE)

( * ) Notice: Subject to any disclaimer, the term of this patent is extended or adjusted under 35 U.S.C. 154(b) by 148 days.

(21) Appl. No.: 10/694,214

(22) Filed: Oct. 28, 2003

(65) Prior Publication Data

US 2004/0131143 A1 Jul. 8, 2004

(30) Foreign Application Priority Data

Oct. 28, 2002 (DE) ................................ 102 50 196

(51) Int. Cl.
*G01T 1/16* (2006.01)
*H01L 27/00* (2006.01)

(52) U.S. Cl. ........................... 250/370.09; 250/363.04; 250/370.15; 378/19; 378/22; 378/4; 378/98.8

(58) Field of Classification Search ........... 250/370.09, 250/363.04, 370.15; 378/19, 22, 4, 98.8
See application file for complete search history.

(56) References Cited

U.S. PATENT DOCUMENTS

| 4,845,731 | A | * | 7/1989 | Vidmar et al. ................. 378/98 |
| 5,103,092 | A | * | 4/1992 | Takahashi et al. ........ 250/252.1 |
| 5,248,885 | A | * | 9/1993 | Sato et al. ............. 250/370.15 |
| 5,799,057 | A | * | 8/1998 | Hoffman et al. ............ 378/147 |

FOREIGN PATENT DOCUMENTS

| DE | 19502574 | | 8/1998 |
| GB | 0302716 A1 | * | 2/1989 |

* cited by examiner

*Primary Examiner*—David Porta
*Assistant Examiner*—Mary Zettl
(74) *Attorney, Agent, or Firm*—Harness, Dickey & Pierce, P.L.C.

(57) ABSTRACT

A detector for X-ray computer tomographs includes a plurality of detector modules which are mounted alongside one another on a frame. Each of the detector modules includes sensor elements for detection of the intensity of incident X-ray radiation. In order to simplify the production of calibration tables, a device for holding a pressure-contact apparatus, provided with a heating element, is provided on the detector so as to face away from the sensor elements.

27 Claims, 4 Drawing Sheets

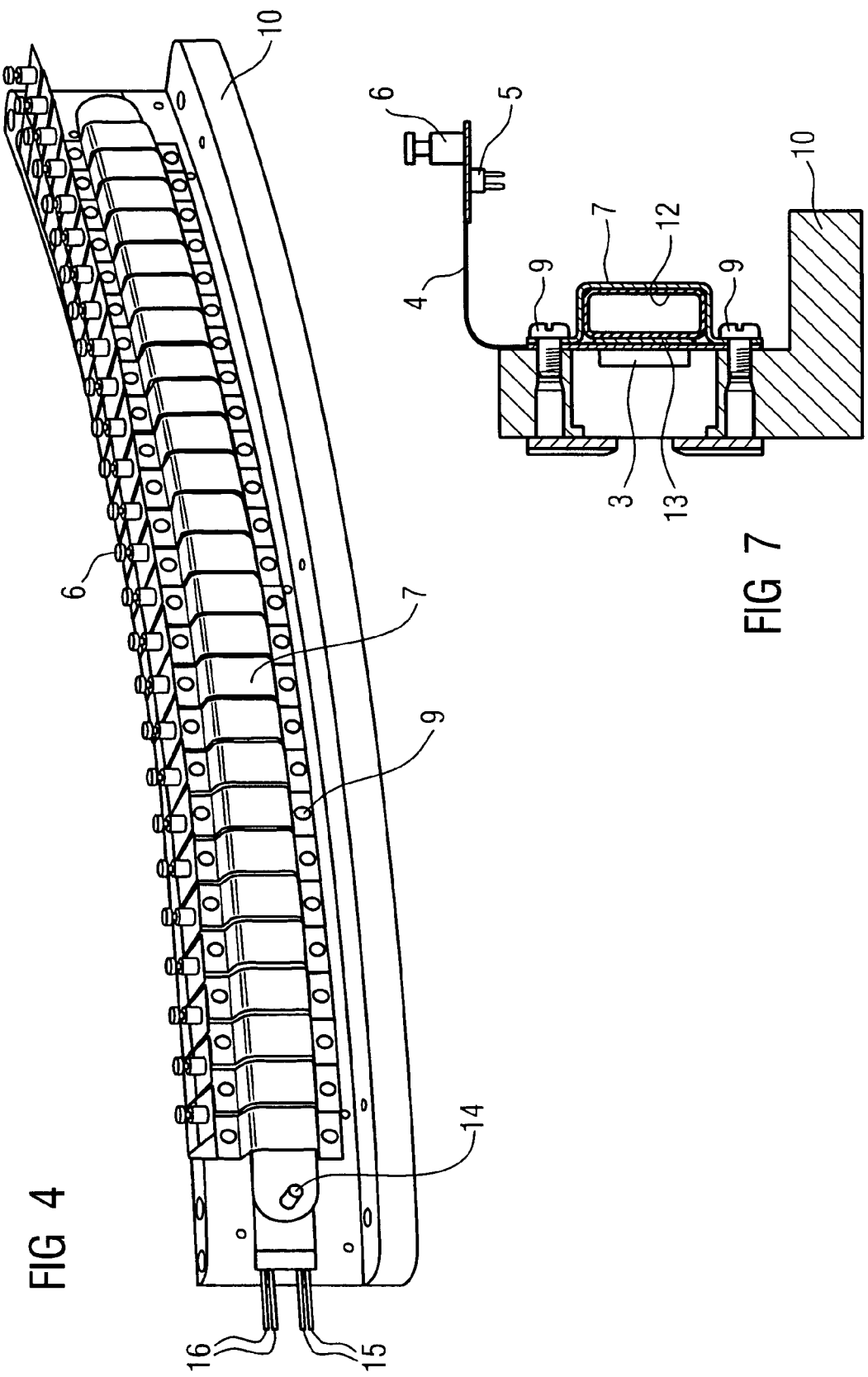

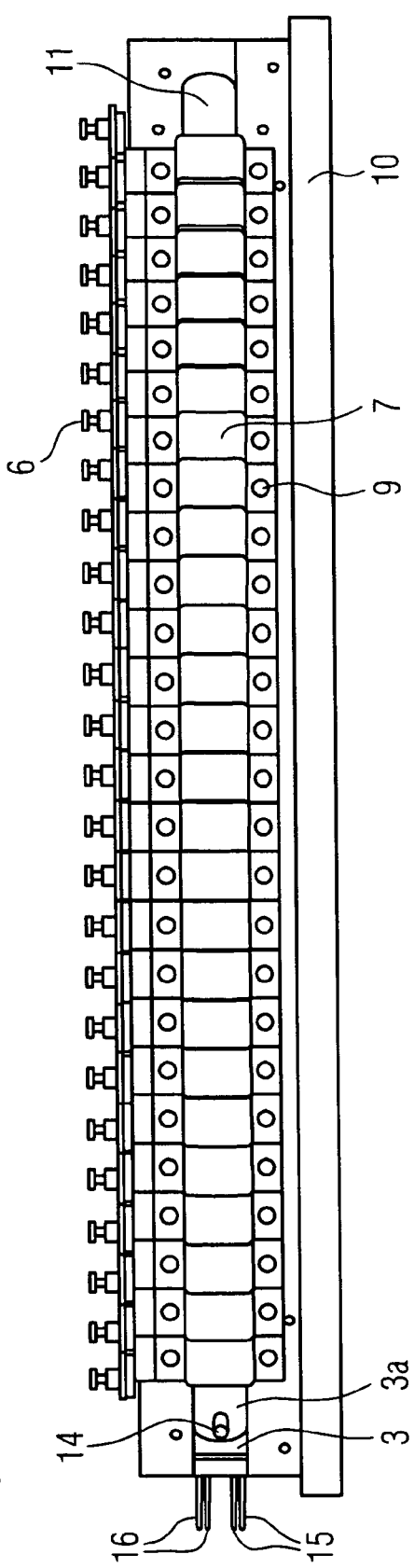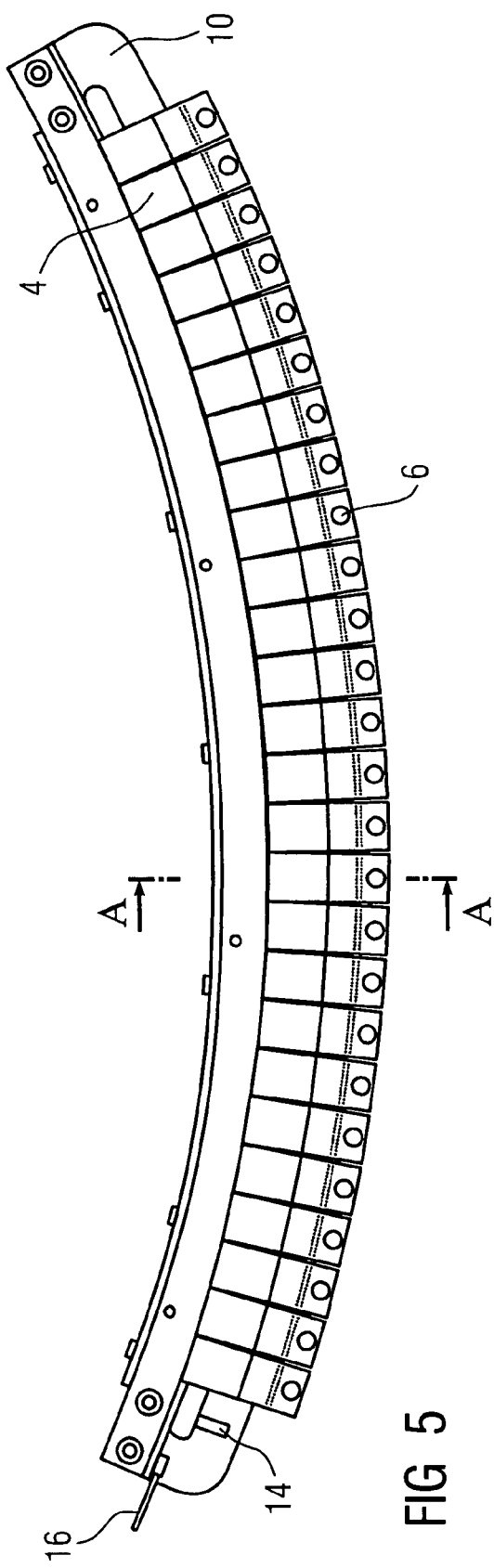

DETECTOR FOR AN X-RAY COMPUTER TOMOGRAPH

The present application hereby claims priority under 35 U.S.C. §119 on German patent application number DE 102 50 196.3 filed Oct. 28, 2002, the entire contents of which are hereby incorporated herein by reference.

FIELD OF THE INVENTION

The invention generally relates to a detector for an X-ray computer tomograph. It also generally relates to a heating apparatus to be held on the detector, and to a method for producing a calibration table for the detector.

BACKGROUND OF THE INVENTION

DE 195 02 574 A1 discloses a detector having two or more parallel detector rows, which run in the direction of the axis of an object, for example a patient, through which X-rays are to be passed. Two or more detector rows may be configured as a mounting unit, for example as a detector module. In this case, a sensor array formed from a large number of sensor elements is mounted on a printed circuit board. The sensor elements have slightly different characteristics. The characteristics of the sensor elements are also dependent on the temperature. In consequence, image artifacts may occur.

U.S. Pat. No. 5,799,057 discloses a detector in which the frame can be heated by means of a heating device. The frame normally has a non-standard temperature emission. It is impossible to ensure that the temperature is constant over all the sensor elements.

A further possible way to avoid image artifacts is to calibrate each sensor element. This can be done by using a special measurement device to produce calibration tables. The calibration tables contain, for example, information about the temperature response, about the radiation drift response, about the relative signal strength, about the persistence response, about the position dependency of the signal strength, about the beam response or defective sensor elements.

In order to produce calibration tables such as these, the detector modules have to be heated to predetermined temperatures by way of a special heating apparatus, and the corresponding calibration data then has to be determined. It is possible, for example, to use an electrical heating cover as the heating apparatus, which is fitted to the rear face of the detector modules. The fitting of a heating cover such as this is time-consuming since the electrical connections between the detector modules and the downstream evaluation electronics must be disconnected first of all. A further problem is that the heating cover does not rest uniformly on all the detector modules. In consequence, the detector modules are not heated to the same temperature.

SUMMARY OF THE INVENTION

An object of an embodiment of the present invention is to overcome the disadvantages of the prior art. A particular aim is to specify a detector for X-ray computer tomographs, which allows calibration tables to be produced easily and at low cost. A further aim of an embodiment of the invention is to provide a heating apparatus which is suitable for this purpose, as well as a method for producing calibration tables using this heating apparatus.

This object is achieved by the features of claims 1, 6 and 12. Expedient refinements of the invention are described in the features of claims 2 to 5, 7 to 11 and 13.

An embodiment of the invention provides that a device for holding a pressure-contact apparatus, which is provided with a heating element, is provided on a rear face of the detector modules facing away from the sensor elements. This allows the heating apparatus to be fitted easily and in less time. The heating apparatus is provided with a pressure-contact apparatus, which ensures that the heating element is pressed uniformly against the rear face of the detector modules. In consequence, all the detector modules can be heated to the same temperature. This avoids the heating element being pressed on non-uniformly. The calibration tables can be produced quickly since, in this case, only the rear face of the detector modules is heated, but not the entire detector frame.

According to one advantageous refinement, the device is a bracket. The bracket and the detector module are expediently mounted on the frame via common attachment elements. The bracket may be produced from metal. The attachment devices are expediently detachable attachment devices, for example screws or the like.

The brackets for detector modules which are mounted on the frame expediently form a channel for the insertion of the pressure-contact apparatus. This allows the pressure-contact apparatus to be inserted into the channel, together with the heating element fitted to it. There is no need to disconnect the electrical connections between the detector modules and the downstream evaluation electronics for this purpose.

According to a further advantageous refinement, the pressure-contact apparatus is an inflatable flexible tube. A pressure-contact apparatus such as this costs little.

Furthermore, to achieve an object, a heating apparatus to be held in the detector according to an embodiment of the invention is provided, in which an elongated pressure-contact apparatus is fitted with a heating element which extends over a major part of its length. The expression a major part of the length means that the heating element extends over at least 60% and preferably 70 to 90% of the length of the pressure-contact apparatus. It is also possible for the heating element to extend over the entire length of the pressure-contact apparatus.

The pressure-contact apparatus is expediently an inflatable flexible tube, at one of whose ends a valve can be fitted. This allows the flexible tube to be inflated easily, and thus allows the heating element to be pressed against the rear face of the detector modules.

The heating element is advantageously provided with at least one temperature sensor, in particular with a thermocouple or with a temperature-dependent resistance. This allows the heating element to be controlled. According to a further refinement, the heating element and/or the temperature sensor are/is adhesively bonded onto an outer face of the flexible tube. The flexible tube is advantageously a flexible silicone tube. Flexible tubes such as these are particularly resistant to temperature.

According to a further refinement, the lines for connection of the heating element and/or of the temperature sensor are routed away at one end. This allows the heating apparatus to be connected easily to a power supply and control device.

Furthermore, according to an embodiment of the invention, a method is provided for producing a calibration table for the detector according to an embodiment of the invention, comprising the following steps:

a) the heating apparatus according to the invention is inserted into the means for holding it, b) the heating element is pressed against the rear face of the detector modules by means of the pressure-contact apparatus, and c) the calibration tables are produced.

The calibration table is produced in the conventional manner, that is to say the heating element is used to heat the detector modules to predetermined temperatures, and their relevant physical parameters are then measured.

The heating element is expediently pressed into contact by inflating a flexible tube which forms the pressure-contact apparatus.

The proposed heating apparatus may remain in the detector after the calibration tables have been produced. The pressure in the flexible tube can be reduced for this purpose. However, it is also possible to release the pressure-contact apparatus after the production of the calibration tables, and to pull the heating apparatus out of the channel. In this case, the heating apparatus can be used for calibration of further detectors.

BRIEF DESCRIPTION OF THE DRAWINGS

The present invention will become more fully understood from the detailed description of preferred embodiments given hereinbelow and the accompanying drawings, which are given by way of illustration only and thus are not limitative of the present invention, and wherein:

FIG. 4 shows a perspective view of a detector,

FIG. 5 shows a plan view corresponding to that shown in FIG. 4,

FIG. 6 shows a side view corresponding to that shown in FIG. 4,

FIG. 7 shows a section view along the section line A—A in FIG. 5,

DETAILED DESCRIPTION OF THE PREFERRED EMBODIMENTS

Figure 1:
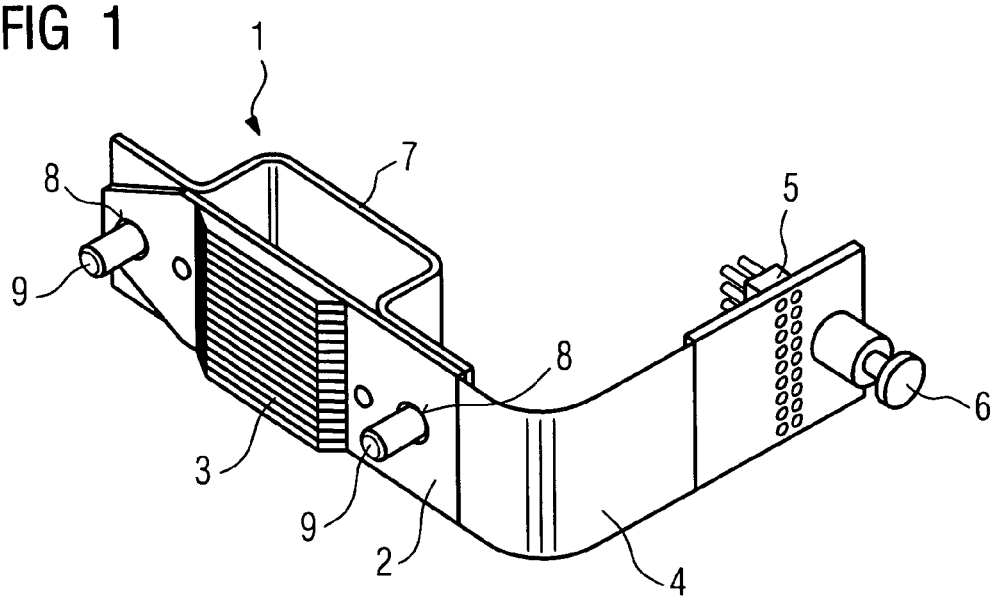
FIG. 1 shows a perspective illustration of a detector module.
Figure 2:
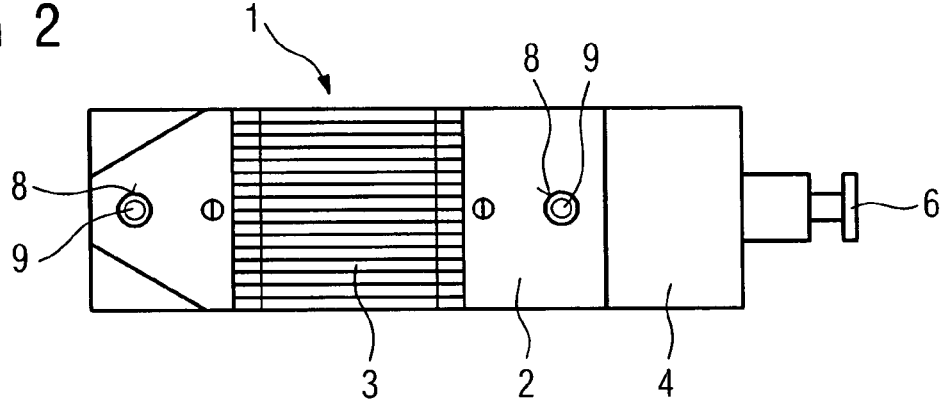
FIG. 2 shows a plan view of the top face of the detector module.
Figure 3:
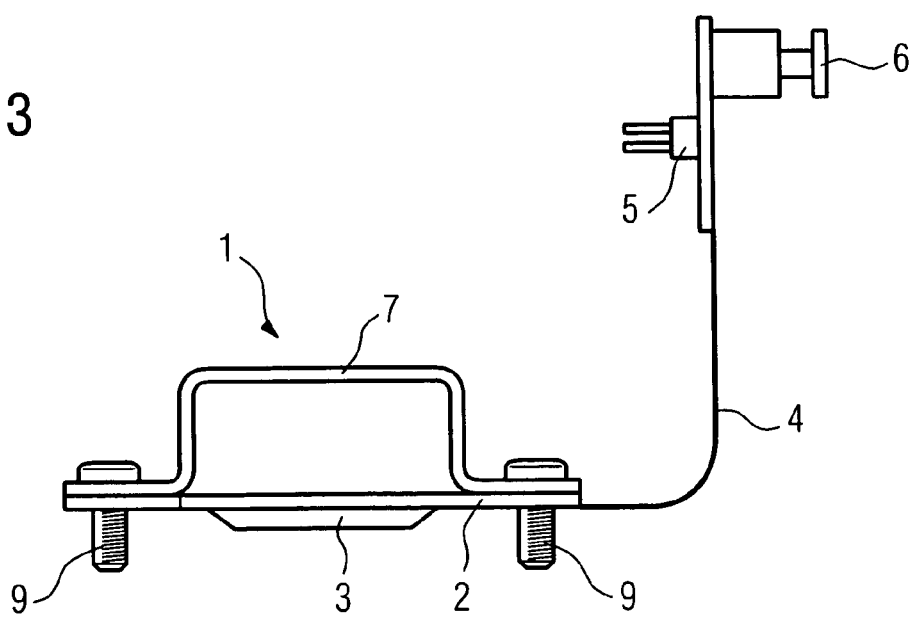
FIG. 3 shows a side view corresponding to that shown in FIG. 2.

FIGS. 1 to 3 show a detector module 1. The detector module 1 has a printed circuit board 2, on whose front face sensor elements 3 are fitted for detection of the intensity of incident X-ray radiation. A flexible connecting strip 4 leads away from the printed circuit board 2, and is provided with a plug 5 at its end. The reference symbol 6 denotes a locking screw, by means of which the plug 5 can be fixed once it has been inserted.

A bracket 7 which is shaped like a U-profile is provided on a rear face of the printed circuit board 2. Apertures 8 which are provided in the bracket 7 and in the printed circuit board 1 are aligned such that the screws 9 can be passed through the apertures 8 in order to mount the bracket 7 and the printed circuit board 2 jointly on a frame (which is not shown here). The bracket 7 is thus fitted to the rear face of the printed circuit board 2 such that its longitudinal side is aligned parallel to the longitudinal extent of the sensor elements 3.

FIGS. 4 to 7 show a detector. In this case, a frame 10 is provided on which a large number of detector modules 1 are mounted alongside one another by way of the screws 9. The brackets 7 which are arranged alongside one another form a curved channel into which a heating apparatus 11 is inserted.

The heating apparatus 11 is shown in detail, particularly in FIGS. 7 to 11. It essentially includes an elongated flexible tube 12 with an essentially rectangular cross section. The flexible tube 12 is advantageously produced from silicone or rubber. A resistance heating element 13 is vulcanized or adhesively bonded onto the flexible tube 12. The resistance heating element 13 extends over the entire length of the flexible tube 12.

At one end of the flexible tube, there is a valve 14 by which the flexible tube 12 can be inflated, and the raised pressure within it can escape. The reference symbol 15 denotes the connections of the resistance heating element 13, while the reference symbol 16 denotes the connections of a temperature sensor (which is not shown here), for example of a thermocouple or of a PT 100. The connections 14, 15 and the valve 14 are expediently arranged at one end of the heating apparatus 11. This makes it easy to connect the flexible tube 12, and to insert it into the channel. The heating element 13 is flexible and is adhesively bonded or vulcanized onto the flexible tube 12.

Figure 8:
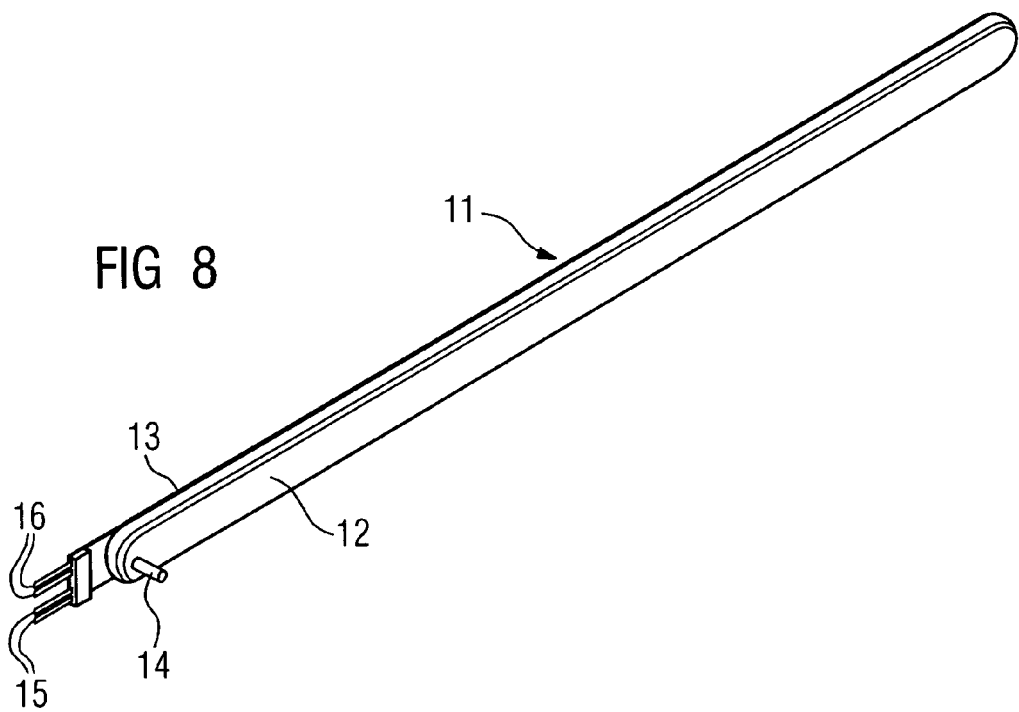
FIG. 8 shows a perspective view of a heating element.
Figure 9:
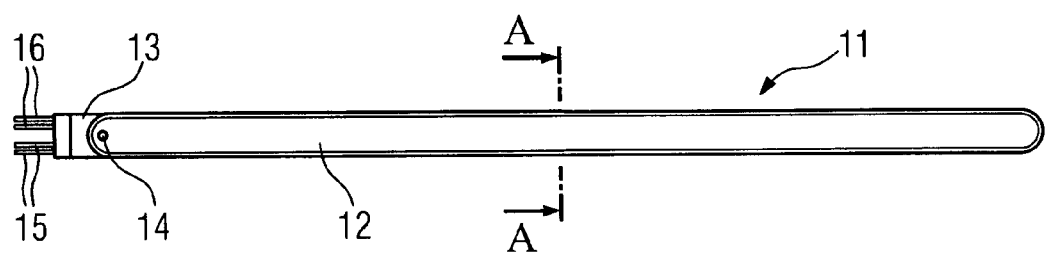
FIG. 9 shows a plan view corresponding to that shown in FIG. 8.
Figure 10:
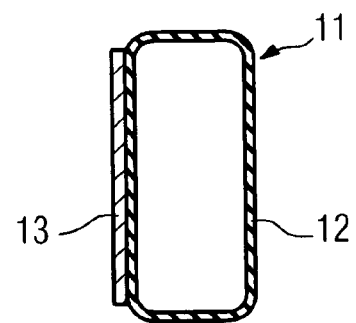
FIG. 10 shows a section view along the section line A—A in FIG. 9.

The proposed apparatus operates as follows:

In order to produce calibration tables, the heating apparatus 11 which is illustrated in FIGS. 8 to 10 is pushed into the curved channel formed from the bracket 7 such that the heating element 13 is pressed against the rear face of the printed circuit board 2. The flexible tube 12 is then inflated by use of the valve 14, so that the heating element 13 is pressed with a uniform pressure against the rear faces of the printed circuit boards 2 of the detector modules 1. Current is then applied to the heating element 13, and it is heated to a predetermined temperature. The temperature is controlled using the temperature sensor (which is not shown here).

The relevant physical parameters are then read from the detector modules, and are recorded in order to produce calibration tables. After recording the calibration data, the pressure in the flexible tube 12 can be released again, and the heating apparatus 11 can be removed. However, it is also possible for the heating apparatus 11 to remain in the detector. In this case, calibration tables can be produced from new once again in a simple manner.

Exemplary embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A detector for an X-ray computer tomograph, comprising:

a plurality of detector modules, mounted alongside one another on a frame, wherein each of the detector modules includes, on its front face, a plurality of sensor elements for detection of an intensity of incident X-ray radiation; and means for holding a pressure-contact apparatus, including a heating element, located on a rear face of the detector modules facing away from the sensor elements.

2. The detector as claimed in claim 1, wherein the means for holding includes at least one bracket.

3. The detector as claimed in claim 2, wherein the at least one bracket and at least one detector module are mounted on the frame by at least one attachment element.

4. The detector as claimed in claim 2, wherein at least two brackets for detector modules mounted on the frame form a channel for insertion of the pressure-contact apparatus.

5. The detector as claimed in claim 4, wherein the pressure-contact apparatus is an inflatable flexible tube.

6. The detector as claimed in claim 1, wherein the pressure-contact apparatus is an inflatable flexible tube.

7. A heating apparatus, adapted to be held in the detector as claimed in claim 1, wherein an elongated pressure-contact apparatus is fitted with a heating element which extends over a major part of its length.

8. The heating apparatus as claimed in claim 7, wherein the pressure-contact apparatus is an inflatable flexible tube.

9. The heating apparatus as claimed in claim 8, wherein the heating element is adhesively bonded onto an outer face of the flexible tube.

10. The heating apparatus as claimed in claim 8, wherein lines for connection of the heating element are routed away at one end of the flexible tube.

11. The heating apparatus as claimed in claim 8, wherein a valve is fitted at one end of the flexible tube.

12. The heating apparatus as claimed in claim 7, wherein a valve is fitted at one end of a flexible tube.

13. The heating apparatus as claimed in claim 7, wherein the heating element includes at least one temperature sensor.

14. The heating apparatus as claimed in claim 7, wherein the heating element includes at least one thermocouple.

15. The heating apparatus as claimed in claim 7, wherein the heating element includes at least one sensor with a temperature-dependent resistance.

16. A method for production of calibration tables for the detector as claimed in claim 1, comprising:
    inserting a heating apparatus into the means for holding;
    pressing the heating element against the rear face of the detector modules by using the pressure-contact apparatus; and
    producing the calibration tables.

17. The method as claimed in claim 16, wherein, once the calibration tables have been produced, the pressure-contact apparatus is released, and the heating apparatus is pulled out of the channel.

18. The method as claimed in claim 17, wherein the pressure-contact apparatus includes a flexible tube, and wherein the heating element is pressed into contact by inflation of the flexible tube.

19. The method as claimed in claim 16, wherein the pressure-contact apparatus includes a flexible tube, and wherein the heating element is pressed into contact by inflation of the flexible tube.

20. The detector as claimed in claim 1, wherein the means for holding and at least one detector module are mounted on the frame by attachment elements.

21. A detector for an X-ray computer tomograph, comprising:
    a plurality of detector modules, mounted on a frame, each of the detector modules including a plurality of sensor elements for detection of an intensity of incident X-ray radiation; and
    at least one bracket, adapted to hold a pressure-contact apparatus, including a heating element, located on the detector modules facing away from the sensor elements.

22. The detector as claimed in claim 21, wherein the at least one bracket and at least one detector module are mounted on the frame by at least one attachment element.

23. The detector as claimed in claim 22, wherein at least two brackets for detector modules are mounted on the frame to form a channel for insertion of the pressure-contact apparatus.

24. The detector as claimed in claim 23, wherein the pressure-contact apparatus includes an inflatable flexible tube.

25. The detector as claimed in claim 21, wherein at least two brackets for detector modules are mounted on the frame to form a channel for insertion of the pressure-contact apparatus.

26. The detector as claimed in claim 25, wherein the pressure-contact apparatus includes an inflatable flexible tube.

27. The detector as claimed in claim 21, wherein the pressure-contact apparatus includes an inflatable flexible tube.

* * * * *